United States Patent [19]
Perez-Aranda Ortega et al.

[11] Patent Number: 4,737,585
[45] Date of Patent: Apr. 12, 1988

[54] PROCESS FOR THE PREPARATION OF SODIUM AMOXYCILLIN

[75] Inventors: Augustin Perez-Aranda Ortega; Santiago C. Ruzafa; Fernando R. Serra, all of Madrid, Spain

[73] Assignee: Antibioticos S.A., Madrid, Spain

[21] Appl. No.: 921,105

[22] Filed: Oct. 21, 1986

[51] Int. Cl.$^4$ ............................................. C07D 499/16
[52] U.S. Cl. ................................... 540/321; 540/323; 540/331
[58] Field of Search ........................ 540/321, 323, 331

[56] References Cited

U.S. PATENT DOCUMENTS 3,262,928  7/1966  Granatek ............................. 540/321
3,669,957  6/1972  Robinson et al. .................... 540/321
4,014,868  3/1977  Berry et al. .......................... 540/323

Primary Examiner—Werren B. Lone
Assistant Examiner—Vera C. Clarke
Attorney, Agent, or Firm—Saidman, Sterne, Kessler & Goldstein

[57] ABSTRACT

Sodium amoxycillin, of use for example by parenteral administration, is prepared by:
(a) suspending amoxycillin trihydrate in a mixture comprising an aprotic organic solvent and a lower alcohol;
(b) solubilizing the amoxycillin trihydrate by the addition of a low molecular weight amine of the group of cyclic or heterocyclic aliphatics;
(c) adding to such solution the sodium salt of diethyloxalacetic acid, agitating the reaction mixture at a temperature of from −10° C. to ambient temperature and finally isolating the sodium amoxycillin by filtration after its precipitation in the reaction medium by the addition of an aprotic organic solvent.

5 Claims, No Drawings

PROCESS FOR THE PREPARATION OF SODIUM AMOXYCILLIN

This invention relates to a process for the preparation of sodium amoxycillin, a broad-spectrum antibiotic and, therefore, of use in medicine for parenteral use.

One of the advantages of amoxycillin is that it is absorbed well when administered per os; however, there are cases in which it is used conveniently by the parenteral route, in which case it must be readily soluble in a sterile pyrogen-free solvent which is the subject of this invention.

Amoxycillin sodium salts can be prepared by the process disclosed by GB No. 1,241,844; however, the resulting yields and purity are low, because, for example, of contamination by penicilloic acid or dimers.

The technology of preparing sodium salts of carboxylic acids and amino acids with the use of sodium hydroxide in an aqueous medium is also known; in the case of the penicillins the method of isolating the salts calls for the use of lyophilization due to the instability of the β-lactam nucleus in the presence of the hydroxy ions, so that the cost of the process is increased. The process according to this invention resides basically in reacting amoxycillin with sodium diethyloxalacetate to form the sodium amoxycillin. Conversion of the amoxycillin with the sodium salts proceeds by evolution of diethyloxalacetic acid, which can readily be moved by washing and dried in vacuo, and the sodium amoxycillin is isolated by filtration of the reaction medium.

For the purposes of the invention the amoxycillin can be used in a trihydrate form and its reaction with the sodium diethyloxalacetate takes place in a reaction medium embodied by a mixture of solvents and in the presence of an organic base.

The reaction with sodium diethyloxalacetate is carried out with quantities which are stoichiometric or slightly greater.

Of the organic bases used to solubilize the amoxycillin trihydrate, amines are selected which are of low molecular weight and which are readily commercially obtainable, such as diethylamine, triethylamine or dicyclohexylamine, all being substantially equivalent to one another in their effects.

The reaction medium is a mixture of solvents comprising a low molecular weight alcohol and a halogenated hydrocarbon or an aprotic solvent such as acetonitrile, methylene chloride, 1,2-dichloroethane or the like. As low molecular weight alcohols there can be used methanol, ethanol, n-propanol, isopropanol, n-butanol or isobutanol.

The process resides in adding to the suspension of amoxycillin trihydrate in the mixture of solvents, a quantity of the organic base, such quantity being stoichiometric or slightly more, then adding the sodium diethyloxalacetate. The mixture is agitated at a temperature of approximately −10° C. to ambient temperature, preferably in the temperature range of from 2° to 15° C. The sodium amoxycillin is isolated by filtration after precipitation in the reaction medium by the addition of a solvent selected from the ketone group, such as methyl ethyl ketone or methyl isobutyl ketone, or by the addition of ethyl acetate or of an alcohol insolubilizing the sodium amoxycillin, such as n-propyl, iso-propyl or iso-butyl alcohol. The selection of any particular solvent depends upon the yield-cost relationship of the process.

One of the advantages of the invention is the preparation of sodium amoxycillin which can be isolated readily by precipitation and filtration, with economic advantages over the conventional lyophilization technologies, and the preparation of sterile sodium amoxycillin, for example, by means of a germicidal filtration before precipitation and drying in a sterile environment.

For a better understanding of the invention some embodiments thereof will be described hereinafter; being explanatory, the embodiments must be regarded as non-limitative in respect of the legal protection requested.

EXAMPLE 1

8.4 g of amoxycillin trihydrate are suspended in a mixture consisting of 120 ml of methylene chloride and 58 ml of n-propanol, 3.3 ml of diethylamine then being added, solution occurring after five minutes. 5.2 g of sodium diethyloxalacetate are then added and are solubilized in the reaction medium, the solution being agitated for 90 minutes in a water-and-ice bath, whereafter 240 ml of methyl isobutyl ketone are added, sodium amoxycillin then starting to precipitate and may be subjected to agitation in the bath for 60 minutes. The precipitate formed is separated by filtration, washed in 30 ml of ethyl acetate and 30 ml methylene chloride and dried in a high vacuum at 3020 C., 6.65 g of sodium amoxycillin being yielded with a potency of 925 mcg. of amoxycillin/mg. (HLPC).

EXAMPLE 2

2.1 g (5 mmol) of amoxycillin trihydrate are added to the mixture of 30 ml of methylene chloride and 10 ml of methanol; after suspension in the reaction medium 0.7 ml (6.6 ml) of diethylamine are added, total dissolution occurring in five minutes. 1.3 g of sodium diethyloxalacetate are then added and the mixture is subjected to agitation for one hour at ambient temperature. 100 ml of ethyl acetate are added to the resulting solution, a white solid being precipitated which is subjected to agitation for 70 minutes, whereafter it is filtered and the solvents washed out, the filtered solid being suspended in 20 ml of ethyl acetate-methanol (6:1) for 15 minutes, whereafter the white solid is filtered, washed in 20 ml of methylene chloride and dried in vacuo at 45° C., for a yield of 1.8 g of sodium amoxycillin of the 100% anhydrous base.

EXAMPLE 3

The procedure of Example 2 is followed but, using 13 ml of ispropyl alcohol instead of the methanol and 40 ml of acetonitrile instead of the methylene chloride, giving 1.8 g of sodium amoxycillin with a potency of 929 mcg. of amocycillin/mg. (HPLC).

EXAMPLE 4

The procedure of Example 2 is followed but using instead of the isopropyl alcohol 17 ml of n-butanol and adding 1 ml of diethylamine. The sodium amoxycillin precipitated is filtered and washed in 25 ml of isopropanol at 30° C., the vacuum-dried solid is suspended in 25 ml of methyl isobutyl ketone with agitation for 15 minutes, then filtered and washed on the filter with 10 ml of methyl isobutyl ketone, then dried in vacuo at 40° C. The yield is 1.8 g of sodium amoxycillin of the 100% anhydrous base.

EXAMPLE 5

2.1 g (5 mmol) of amoxycillin dihydrate are suspended in 40 ml of chloroform and 22 ml of isopropanol, 0.9 ml (8.6 mmol) of diethylamine then being added, total dissolution of the antibiotic occurring after 2 minutes, whereafter 1.3 g of sodium diethyloxalacetate are added and the solution is maintained in agitation at ambient temperature for 2 hours, whereafter 140 ml of methyl isobutyl ketone are added, agitation continuing at 5° C. for 90 minutes. The precipitate formed is separated by filtration, washed in 20° C. of ethyl acetate and 20° C. of methylene chloride, then dried in vacuo at 35° C., the resulting product being anhydrous sodium amoxycillin with a potency (HPLC) of 919 mcg of amoxycillin/mg, $[a]^{20} = +224°$ C., c=1% in water.

EXAMPLE 6

2.1 g of amoxycillin trihydrate were suspended with agitation in a mixture consisting of 40 ml of methyl chloride, 18 ml of methanol and 1 ml of triethylamine, total solution occurring after 10 minutes, whereafter 1.25 g of sodium diethyloxalacetate are added, the dissolution being observed in 5 minutes. The solution is agitated for 100 minutes at ambient temperature, whereafter 150 ml of methyl isobutyl ketone are added, yielding a white precipitate which is filtered and suspended in 25 ml of methyl isobutyl ketone for 15 minutes, then filtered and dried in vacuo. A white solid is obtained which turns out to be the sodium salt of amoxycillin, distinguished by IR, UV c=20 mcg/ml in water, $A_{272}=0.651$, $A_{259}=0.528$.

EXAMPLE 7

The procedure of Example 6 is followed but with 25 ml of isobutanol instead of the methanol and 1.4 ml of diethylamine instead of triethylamine; a white solid is obtained which is determined to be sodium amoxycillin by virtue of its IR and UV spectrum, with a yield of 70% of sodium amoxycillin on an anhydrous base.

EXAMPLE 8

The procedure of Example 2 is followed, but using 1.2 ml of dicyclohexylamine instead of the diethylamine. A white solid is obtained which after drying in vacuo in a nitrogen atmosphere and on $P_2O_5$ has a microbiological potency of 932 mcg of amoxycillin/mg. The yield is 74.3% of sodium amoxycillin as anhydrous base.

Now that the description to which the previous specification refers has been made, it must be emphasised that details of implementation of the idea explained may vary.

We claim:

1. A process for the preparation of sodium amoxicillin, of use for parenteral administration, comprising:
    (a) suspending amoxicillin trihydrate in a mixture of comprising an aprotic organic solvent and a lower alcohol;
    (b) solubilizing the amoxicillin trihydrate by the addition of a low molecular weight amine;
    (c) adding to such solution the sodium salt of diethyloxalacetic acid,
    (d) agitating the reaction mixture at a temperature of from $-10°$ C. to ambient temperature, and
    (e) isolating the sodium amoxicillin by filtration after its precipitation in the reaction medium by the addition of an aprotic organic solvent.

2. A process for the preparation of sodium amoxicillin according to claim 1 wherein the amoxicillin trihydrate is suspended in an aprotic organic solvent selected from the group consisting of acetonitrile methylene chloride, chloroform and 1,2-dichloroethane.

3. A process for the preparation of sodium amoxicillin according to claim 1 wherein the aliphatic alcohol is selected from the group consisting of methanol, ethanol, n-propanol, isobutanol, ispropanol and n-butanol.

4. A process for the preparation of sodium amoxicillin according to claim 1, characterized in that the amoxicillin trihydrate is solubilized by the addition of an amine selected from the group consisting of diethylamine, triethylamine and dicyclohexylamine.

5. A process for the preparation of sodium amoxicillin according to claim 1 wherein the sodium amoxicillin is isolated by the addition of an aprotic organic solvent selected from the group consisting of ethyl acetate, methyl isobutyl ketone, and methyl ethyl ketone and by subsequent filtration and drying.

* * * * *